(12) United States Patent  
Bailey et al.

(10) Patent No.: US 10,617,375 B2
(45) Date of Patent: Apr. 14, 2020

(54) C-ARM WITH INTEGRATED CT SYSTEM (71) Applicant: Dedicated2Imaging, LLC, Portsmouth, NH (US)

(72) Inventors: Eric M. Bailey, North Hampton, NH (US); Andrew Tybinkowski, Silver Lake, NH (US)

(73) Assignee: Dedicated2Imaging, LLC, Portsmouth, NH (US)

( * ) Notice: Subject to any disclaimer, the term of this patent is extended or adjusted under 35 U.S.C. 154(b) by 0 days.

(21) Appl. No.: 16/073,882

(22) PCT Filed: Apr. 11, 2017

(86) PCT No.: PCT/US2017/026920
§ 371 (c)(1),
(2) Date: Jul. 30, 2018

(87) PCT Pub. No.: WO2017/180569
PCT Pub. Date: Oct. 19, 2017

(65) Prior Publication Data
US 2019/0038245 A1  Feb. 7, 2019

Related U.S. Application Data (60) Provisional application No. 62/320,624, filed on Apr. 11, 2016.

(51) Int. Cl.
A61B 6/03  (2006.01)
A61B 6/00  (2006.01)
A61B 6/06  (2006.01)

(52) U.S. Cl.
CPC ............ *A61B 6/4417* (2013.01); *A61B 6/035* (2013.01); *A61B 6/06* (2013.01); *A61B 6/4007* (2013.01); *A61B 6/4014* (2013.01); *A61B 6/4283* (2013.01); *A61B 6/4441* (2013.01); *A61B 6/487* (2013.01); *A61B 6/5235* (2013.01)

(58) Field of Classification Search
CPC .............................. A61B 6/035; A61B 6/4441
See application file for complete search history.

(56) References Cited

U.S. PATENT DOCUMENTS

| 7,170,974 | B2 * | 1/2007 | Groh ........................ A61B 6/00 378/197 |
| 7,609,808 | B2 | 10/2009 | Tornai et al. |
| 8,831,173 | B2 * | 9/2014 | Uehara ................ A61B 6/4021 378/116 |
| 9,001,962 | B2 * | 4/2015 | Funk ...................... A61B 6/032 378/196 |
| 2003/0002626 | A1 | 1/2003 | Hoheisel et al. |
| 2009/0257551 | A1 | 10/2009 | Dafni et al. |
| 2011/0096894 | A1 | 4/2011 | Uehara et al. |
| 2011/0280380 | A1 | 11/2011 | Maschke |
| 2014/0177785 | A1 | 6/2014 | Funk |
| 2015/0196261 | A1 * | 7/2015 | Funk ...................... A61B 6/032 378/9 |

* cited by examiner

*Primary Examiner* — Thomas R Artman (57) ABSTRACT

A hybrid imaging system is disclosed including an arcuate arm defining a first and a second end the arcuate arm including a first detector assembly for 2D x-ray imaging of a patient and a second detector assembly for CT imaging of the patient, wherein the imaging system includes an internal drive mechanism for rotating the arcuate arm (e.g. translating the arcuate arm along an arcuate path) around the patient.

20 Claims, 6 Drawing Sheets

C-ARM WITH INTEGRATED CT SYSTEM

CROSS-REFERENCE TO RELATED SECTIONS

The subject application claims the benefit of U.S. Provisional Application Ser. No. 62/320,624 filed Apr. 11, 2016 and entitled "C-Arm With Integrated CT System," the contents of which are hereby incorporated herein in their entirety.

BACKGROUND

The subject application relates to portable imaging systems, such as mobile fluoroscopic systems also generally known as portable C-Arms, which may be utilizing e.g., in an operation room. In particular, new and improved portable imaging systems are disclosed which provide for both hybrid flat panel x-ray imaging and computerized tomography (CT) imaging. The disclosed systems and methods have significant implications and applicability with respect to the fields of surgical imaging as interventional radiology.

Imaging plays a big role today in many surgical theaters including but not limited to neurosurgical spine and brain, orthopedic knee and hip, urological prostate and kidney, trauma (ER), etc. To date these surgeries have relied upon 2D X-ray or ultrasound imaging during surgery, and 3D CT and/or MRI both pre and post surgery. This is due primarily to the fact that it has been difficult to put a conventional CT or MRI into an operating room (OR). Conventional CT and MRI are both very large, require the patient to be moved into a bore, and have physical properties such as radiation and strong magnetic fields that cause concerns and compromise. However in the last 10 years we have seen the advancement of portable CT scanners, which can be manipulated in ORs. But even though these scanners have proven as breakthrough technology, they have not replaced the utility of 2D X-ray during major portions of the surgery where temporal resolution is required such as during the active insertion of an object. 2D fluoroscopy gives excellent temporal resolution under foot control of the surgeon. 2D images also are much lower in total radiation dose, which is good for both the patient and the surgical staff. But there are key times in the surgery where a 3D high quality CT image is both required and appreciated. In spine surgery this 3D image is used to confirm the angle of pedicle screw insertion and also to confirm correct placement after insertion of hardware.

Thus it would be optimal for surgeons to have OR access to both a 2D X-ray C-Arm and a high quality CT scanner. Existing portable CT scanners by Samsung/Neurologica and Mobius/Brainlab, however, do not have 2D C-Arm capability and thus make the surgical field very crowded and awkward to bring in another machine. The O-Arm system by Medtronic does have 2D and 3D capability but the CT quality is via a pseudo flat panel CT which is poor contrast resolution, small field of view, and bountiful with artifacts such as streaks. The O-arm 2D x-ray system also lacks the freedom of image angles and produces poorer image quality than conventional C-arms. Finally, while several C-arm manufacturers have enabled their C-arms to rotate and produce a CT-like image (such as the Siemens Orbic 3D) these systems suffer from the same image quality issues of the O-arm.

Thus, what is missing from the marketplace and what surgeons really desire one machine that can both act as a 2D X-ray C-arm and a high quality CT. Ideally such a machine maintain the special freedom of the C-arm, have high quality contrast resolution CT for a small longitudinal scan length, and have the ability to register with the surgical table for repeat scans later in the surgery that must be taken from the same position. Thus, there exists a need for improved portable hybrid imaging systems, which are capable of providing both CT and x-ray imaging with high quality while maintaining the maneuverability and ease of use of a traditional C-Arm. These and other needs are addressed by the systems disclosed herein.

SUMMARY

In example embodiments, a hybrid imaging system is presented including an arcuate arm defining first and second ends and including one or more x-ray generation assemblies, a first detector assembly for 2D-imaging of a patient and a second a second detector assembly for CT imaging of the patient, wherein the imaging system includes an internal drive mechanism for rotating the arcuate arm around the patient. For example, rotating the arcuate arm may include translating the arcuate arm along an arcuate path. Alternatively, rotating the arcuate arm may include rotating the arm around a pivot point. In some embodiments, the first detector assembly is a flat-panel detector assembly, which may be configured for fluoroscopic imaging of the patient, and the second detector assembly may be an arcuate detector assembly (e.g., including a plurality of arcuate rows of detector elements in a detector array), which may be configured for a modified form of CT imaging. In preferred embodiments, the second detector assembly may define a detection width of greater than 3 cm to enable CT imaging of a wide slice with a single rotational pass.

In some embodiments, the hybrid imaging system may be configured to enable selective deployment of the first and second detector assemblies with respect to a detection region of the arm. Thus, for example, the x-ray generation assemblies may be included at an x-ray generation region of the arm wherein the detection region is at a first end of the arm and the x-ray generation region is at a second opposite end of the arm. The hybrid imaging system may advantageously enable selection of an imaging mode whereby a corresponding one of the detection assemblies is deployed with respect to the detection region. In some embodiments, at least one of the detection assemblies is retractably deployable with respect to a detection region of the arm. For example, one of the detector assemblies may be permanently fixed with respect to the detection region of the arm while the other detector assembly is retractably deployable. Thus, in some embodiments, the first detector assembly may be permanently fixed with respect to the detection region while the second detector assembly may be configured to be retractably deployable over the first detector assembly (e.g., by translating, rotating, pivoting, swinging or otherwise moving between retracted and deployed positions). In example embodiments, the retractably deployable detector assembly may translate in an arcuate manner along an inner arcuate inner surface of the arm between the retracted and deployed positions. Alternatively, the retractably deployable detector assembly may translate sideways between retracted and deployed positions. Note that in some embodiments, both detector assemblies are retractably deployable. Thus, in some embodiments, the first and second detector assemblies may be fixed relative to one another and movable between a first position where one of the detector assemblies is deployed and a second position where the other detector assembly is deployed (e.g., the first and second detector assemblies may be fixed side-by-side relative to one another and may be configured for sideways translation thereof to enable selective deployment of one or the other of the detector assemblies.

In further example embodiments, the one or more x-ray generation assemblies may include a hybrid x-ray generation assembly which includes a hybrid collimator enabling selective switching back and forth between 2D and CT exposure modes. In other embodiments, a first x-ray generation assembly may include a first collimator configured for a 2D exposure mode and a second x-ray generation assembly includes a second collimator configured for a CT exposure mode.

BRIEF DESCRIPTION OF THE DRAWINGS

The present disclosure is further described in the detailed description which follows, in reference to the noted plurality of drawings by way of non-limiting examples of embodiments of the present disclosure.

DETAILED DESCRIPTION

In example embodiments, a hybrid imaging system is disclosed including an arcuate arm defining a first and a second end the arcuate arm including a first detector assembly for 2D x-ray imaging of a patient and a second detector assembly for CT imaging of the patient, wherein the imaging system includes an internal drive mechanism for rotating the arcuate arm around the patient (e.g. by either translating the arcuate arm along an arcuate path or by rotating the C-arm about a rotational axis at a pivot connection point along the arcuate path of the C-arm). The hybrid imaging system may further include one or more x-ray generation assemblies.

In some embodiments, the first detector assembly may be a flat-panel detector assembly. In further embodiments, the first detector assembly may be configured for fluoroscopic imaging of the patient.

In example embodiments, the second detector assembly may be an arcuate detector assembly. For example, the detector assembly may include a plurality of arcuate rows of detector elements in a detector array. Advantageously the second detector assembly may define a detection width of greater than 3 cm or greater than 4 cm, e.g., to enable CT imaging of a wide slice with a single rotational pass.

Advantageously, the hybrid imaging system may be configured to enable selective deployment of the first and second detector assemblies with respect to a detection region of the arm, e.g., at the first end of the arcuate arm. That is to say that the hybrid imaging system may allow for a user to select an imaging mode whereby the appropriate corresponding detection assembly is deployed with respect to a common detection region at the first end. Thus, at least one of the detection assemblies may be retractably deployable with respect to the detection region of the arm.

Figure 1:
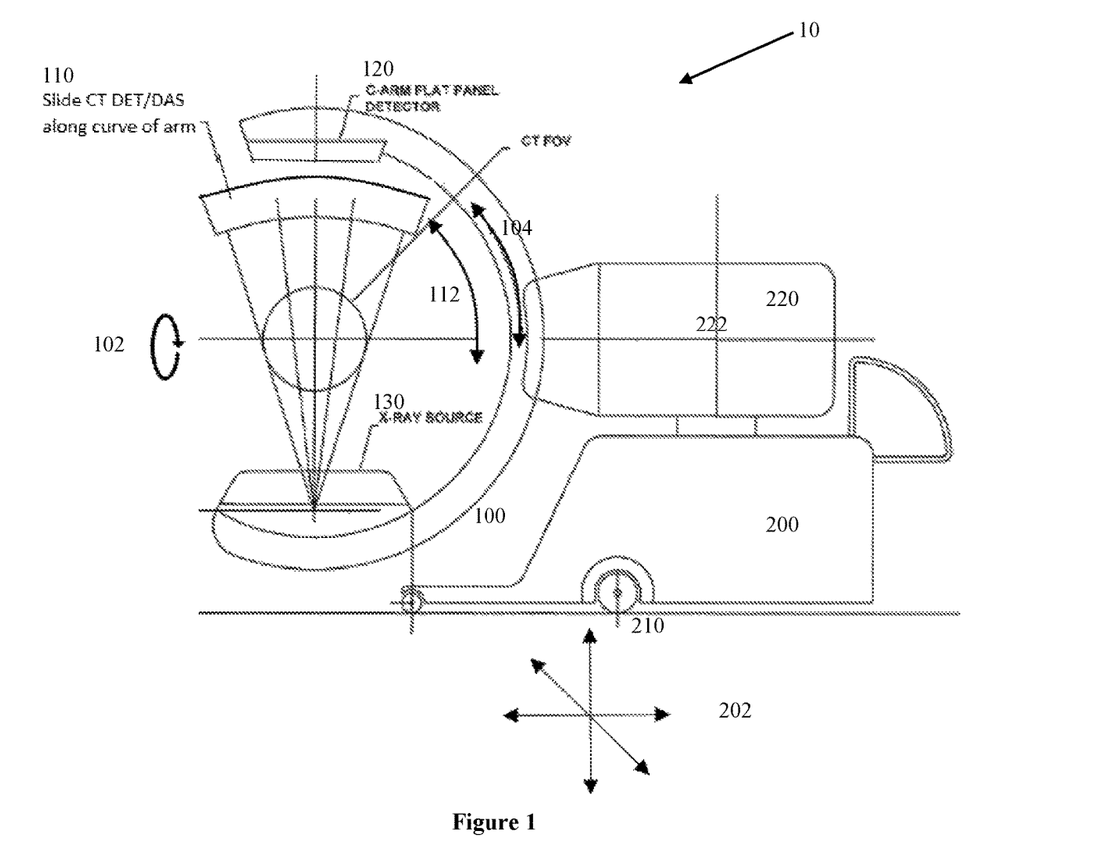
FIG. 1 depicts an example hybrid imaging system, according to embodiments of the present disclosure.
Figure 2:
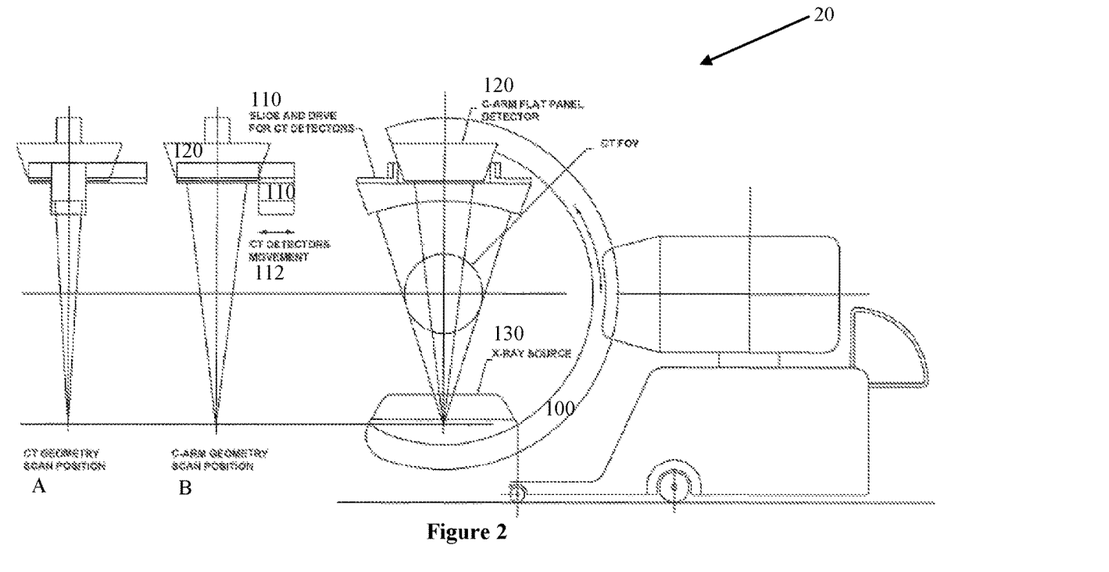
FIG. 2 depicts a variation of the hybrid imaging system of FIG. 1, illustrating an alternative mechanism for deploying a CT detection assembly, according to embodiments of the present disclosure.

In some embodiments, one of the detector assemblies may be permanently fixed or static with respect to the detection region of the arm while the other detector assembly may be retractably deployable. For example, in some embodiments the first detector assembly may be permanently fixed with respect to the detection region arm while the second detector assembly may be configured to be retractably deployable over the first detector assembly. In exemplary embodiments, the retractably deployable detector assembly may translate, rotate, pivot, swing or otherwise move between retracted and deployed positions. For example, in some embodiments, such as shown with respect to FIG. 1, the retractably deployable detector assembly may translate in an arcuate manner along an inner arcuate surface of the arm between retracted and deployed positions. Alternatively, as depicted in FIG. 2, the retractably deployable detector assembly may translate sideways between retracted and deployed positions. It should be noted, however, that the present disclosure in not limited to the depicted embodiments, and that other mechanism for retractably deploying the detector assembly may be utilized without departing from the scope hereof.

In some embodiments, both detector assemblies may be retractably deployable. In some embodiments, the first and second detector assemblies may be fixed relative to one another and movable between a first position where one of the detector assemblies is deployed and a second position where the other detector assembly is deployed. For example, the first and second detector assemblies may be fixed side-by-side, relative to one another and may be translated back and forth sideways to deploy the appropriate detector assembly. In other embodiments, the first and second detector assemblies may be movable independent of one another.

In example embodiments, the x-ray generation assembly may be reconfigurable depending on the imaging mode (e.g., with different collimators, beam characteristic and/or power profiles for x-ray generation depending on imaging mode). In some embodiments, one or more x-ray generation assemblies may be included at an x-ray generation region of the arm. In some embodiments, the one or more x-ray generation assemblies may include a hybrid x-ray generation assembly which includes a hybrid collimator which enable selectively switching back and forth between 2D and CT exposure modes. Alternatively in some embodiments, a first x-ray generation assembly may be included including a first collimator configured for a 2D exposure mode and a second x-ray generation assembly may be included including a second collimator configured for a CT exposure mode.

In order to have a single X-ray source to be useful for both X-ray fluoroscopy and CT imaging it is beneficial enable changing x-ray collimation. X-ray fluoroscopy generally utilizes a square-like beam of radiation to be generated in order to produce an umbra of x-rays onto an x-ray detector plate on the opposite side of the C-arm (typical dimension could be 30×30 cm). It thus optimally utilizes a collimator made from high density material with a square opening. In contrast, in some embodiments, the proposed CT detector is a long curved sensor, which optimally utilizes a collimator made from high density material with a long bowtie shaped opening. One method for providing a hybrid x-ray generation assembly is to have two different collimator plates that are shuttled in and out of the x-ray beam for respective X-ray fluoroscopy/CT imaging modes.

In generating x-rays for different medical imaging systems there are many basic commonalities:

X-ray tube: a sealed evacuated vessel that contains a cathode and anode. A high voltage potential (>30 kiloVolts) is placed across the cathode/anode. Some source of available electrons are supplied by something called a filament. High energy electrons then fly from the cathode to anode and collide with the anode. Some of these high speed collisions produce x-ray photons. These photons are then allowed to escape the tube through some "window" where they are aimed at a target, normally some type of detector. The focal spot generates heat that must be removed by some type of cooling method. Higher power tubes may benefit from a rotating anode to prevent focal spot melting of the anode.

High Voltage Power Supply (HVPS): A method to generate the high voltage. Normally a DC output. It will generally consist of some type of main power system which will pre-condition and pre-amplify the mains power into some intermediate level of high voltage (2-3 kilovolt). It then consists of a high voltage "tank" which consists of some type of high voltage amplifier such as a "Villard cascade" of diodes and capacitors normally built in some type of ladder approach. This tank must contain high voltage insulation system which is generally some type of dielectric oil or a high voltage dielectric polymer.

Filament and cup: a small diameter coil of wire whereby a high current is passed allowing it to create emission of photons. A "cup" is surrounded to allow for a shaping of the beam to create the size of the focal spot. Because the filament takes time to heat up, there is usually an amount of time for filament preheating before the x-ray exposure. Filament current is then relative to the ultimate x-ray tube current which is proportional to the amount of x-ray photons flux. A tube can have multiple focal spots.

Focal spot: The area whereby the electrons that collide into the anode. This creates the physical size of the emitted x-rays. This size is important in achieving certain spatial resolution in the images. Because most of the collisions create heat, the spot is also limited in how small one can make it for a given emission profile due to cooling limitations.

Control system: This circuitry can be simple or very complex, depending on the type (CT or X-ray) or sophistication of the model of machine. The control system is necessary to set the KV (kilovolt level) and the mA (x-ray tube current). It controls the timing for x-ray emission and has safety circuitry for shutting down x-rays. It has a filament circuit that provides a small voltage and large current to a filament to produce x-ray emission. Sophisticated supplies have servo loops whereby KV and mA feedback are used to servo filament current and KV levels to achieve a more accurate x-ray emission profile.

Cooling system: Some type of way to cool the x-ray anode. Higher power medical x-ray tubes have a liquid (dielectric oil or water) cooling system which pumps liquid through the tubes' cooling orifices and back into a heat exchanger system consisting of a radiator and fan.

High voltage cable(s): A well-insulated cable and connector are beneficial to bring the high voltage connections from the HVPS to the x-ray tube.

While CT and diagnostic x-ray generally use the same types of components listed above, there are many subtle differences in their emission characteristics that generally require different construction of the components. The following section compares some of these differences:

CT typically is characterized by much higher KV levels (120-140 KV) vs. standard x-ray (60-90 KV).

CT also benefits from very accurate KV levels because small changes in KV can result in artifacts in the images. CT has to calibrate its machine for all desired KV levels. Standard x-ray does not have this severe sensitivity. CT thus typically has a more sophisticated control circuitry and capacitive filtering.

CT generates x-rays for prolong times (1-60 seconds) in a steady state fashion whereby standard x-ray is normally used in a pulsed form whereby pulse widths are short (100 mS-1 sec).

Standard X-ray generally has smaller focal spots for the higher resolution required and provided by high definition detectors or film. CT focal spots are larger because spatial resolution is less but heating is higher thus benefitting from a larger spot.

Since this hybrid imaging systems are presented herein it is advantageous to provide an X-ray generator topology that addresses different requirements on both x-ray beam profiles.

A simple solution is to have two separate x-ray generation systems with its own tube, HVPS, and control.

Another solution is to have one x-ray tube that contains two different filaments (one for CT, one for x-ray) that is powered by a HVPS that has two different high voltage and control circuits to generate the two profiles. This solution takes up less space and is less expensive and complex. Moreover, it advantageously utilizes common main power and control system, but also contains two specific control and high voltage circuits. Only one high voltage system is energized at one time.

Figure 3:
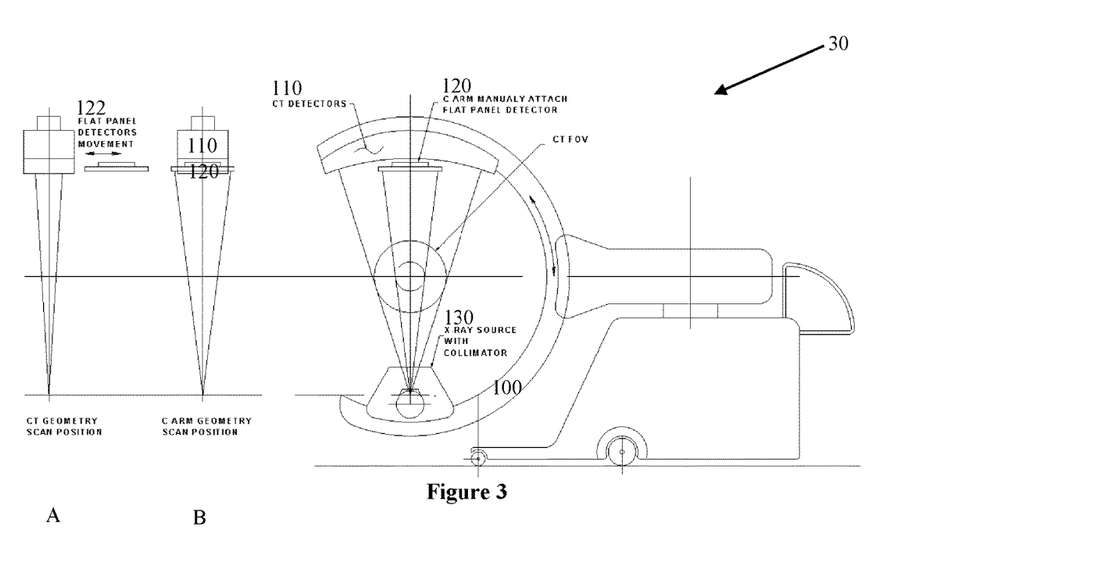
FIG. 3 depicts a further variation of the hybrid imaging system of FIG. 1, illustrating that in some embodiments, a flat panel x-ray detector may be moved rather than a CT detector assembly to switch between imaging modes, according to embodiments of the present disclosure.
Figure 4:
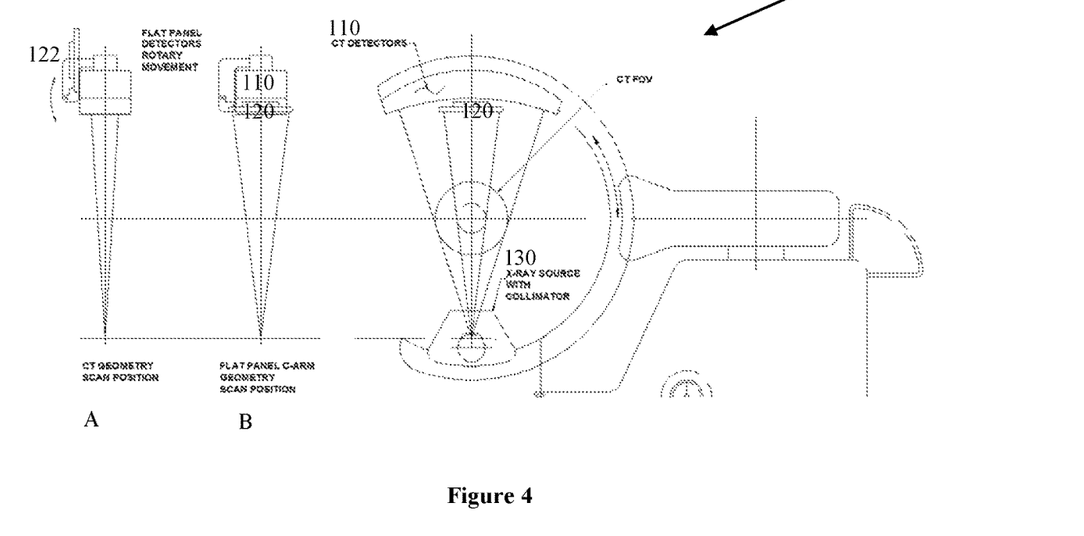
FIG. 4 depicts a further variation of the hybrid imaging system of FIG. 1, illustrating that in some embodiments, a flat panel x-ray detector may be moved by pivoting it away from a CT detector assembly to switch between imaging modes, according to embodiments of the present disclosure.

In example embodiments, the systems and methods disclosed herein advantageously propose a new CT-enabled C-Arm system with a retractable CT detector assembly that can be deployed for performing a CT scan, and moved out of the way of a traditional flat panel x-ray detector when wanting to perform standard 2D x-ray imaging. In example embodiments, such as depicted in FIG. 1, the CT detector assembly may be deployed by translating the CT detector assembly along the arcuate length of the C-Arm. Thus, in some embodiments the detector assembly may be an arcuate or banana shaped detector assembly, e.g., configured to translate along an arcuate path around an inner arcuate surface of the C-Arm. In other embodiments, such as depicted in FIG. 2, the CT detector assembly may be deployed by translating, pivoting, swinging or otherwise moving the CT detector assembly into position. The CT-enabled C-Arm may further include an x-ray generation system including a new type of collimator may be added that will be able to provide x-ray beams for both 2D and CT detectors. Furthermore the new scanner may be mechanically integrateable with one or more surgical tables for accurate image registration. In further example embodiments, such as depicted in FIG. 3 the CT detector assembly may be deployed by removing a flat panel detector thereby exposing a CT detector underneath. In yet further example embodiments, such as depicted in FIGS. 4A and 4B, the C-arm may be configured to support a first beam bath for x-ray type imaging and a second beam path for CT type imaging. Thus, in some embodiments, a first end of the C-arm may include an flat panel x-ray detector and a CT type detector assembly slightly offset from one another along the arcuate surface of the C-arm. Corresponding x-ray generation assemblies (e.g., specific to flat panel x-ray imaging or CT imaging) may be positioned across from their respective detectors at a second end of the C-arm again offset from one another along the arcuate surface of the C-arm. In other embodiments respective x-ray and CT type detectors may be positioned on opposing ends of the C-arm, each opposite a corresponding x-ray generation assembly which is on the same side as the other detector type. In example embodiments, the CT detector may advantageously be configured to provide good longitudinal coverage (3-4 cm or greater) to be able to image an important area of the surgical field, without requiring stepping translation. In some embodiments, cross-registration may be enabled between respective CT and x-ray imaging modes. Thus, in some embodiments, 3D CT imaging data may be supplemented by higher definition 2D x-ray imaging data to provide a more complete anatomical picture to a care provider. In some embodiments, cross-registration of imaging may be used to implement active guidance for a surgical process (surgical navigation).

Advantageously, the proposed CT-enabled C-Arm may also be useful with respect to Interventional Radiology markets. Many IR procedures such as biopsies are accomplished with a fixed CT scanner. The procedure involves many consecutive CT scans creating high radiation exposure levels. In addition patients are adapted to CT tables, which are less than optimum for these surgical-like procedures. The patient must also be moved on the translating table in and out of the gantry, which creates safety hazards, delays, and possible movement of patient or needle. The proposed CT-enabled C-Arm can be the elegant solution to all of these problems and increase the safety and efficacy of IR procedures. An optimum patient table(s) needs to be selected which better fit the procedures and patient positioning that are required.

Interventional Radiography is a very widely used medical practice used for navigating treatments and/or diagnostics into a very specific location within a patient's body. Examples of treatments are injecting medicines for pain treatment in areas like the spine, or placing drains around abscesses. A major example of diagnostic usage is to perform a biopsy on a deeply positioned mass or lesion. These procedures contain many possible hazards such as:

Avoiding injury to potential organs or blood vessels that are in the path or adjacent to the targeted area.

Excess radiation during the procedure carries risks such as cancer, cataracts, etc. This hazard also affects the Medical staff and physician.

May require general anesthesia for long periods of time.

Mechanical hazard to the patient during procedure in the process of shuttling a patient in and out of a CT scanner numerous times during the procedure.

The hazard that the specific target is missed during the procedure resulting in the wrong biopsy results, missed therapy, etc.

Multiple entry sites or attempts all compensating for missed targeting or to require insurance against false results.

Considerable amount of time to move patients back and forth and waiting on radiology for CT imaging thus increasing the cost of the procedure and limiting the number of possible procedures per day for a given treatment setup. In addition the conventional CT imaging systems require a large amount of space thus taking up more expensive hospital real estate.

These hazards and detriments exist as described above because many of the procedures rely on use of a traditional CT scanner. An example of the present state of the art workflow for an Interventional Radiology guided biopsy of a suspicious lesion in the liver is as follows:

Patient positioned on CT table and anesthetic administered.

Patient repositioned to expose the entry site and allow the proper trajectory for biopsy (CT tables make it difficult to correctly position patients in the supine position).

Patient scanned inside CT and brought back out.

Patient repositioned. Scan again. Repeat until position is correct.

Partial insertion of biopsy needle.

Patient shuttled into scanner and scanned to determine if entry site correct. Repeat if necessary.

Further insertion of needle, shuttle in, scan, shuttle out, repeat.

Finally the targeted area is reached. And biopsy achieved.

This process can result in numerous scans (>30). CT scans generate a very high amount of radiation both to the patient and personnel. The physician is especially susceptible as they perform this method every day, thus requiring the use of shields/lead vests/etc. CT scans also take a long time to perform and therefore cannot provide real time imaging during a surgical procedure. Moreover, while standard x-ray imaging such as x-ray fluoroscopy (achieved with a conventional x-ray C-arm) can be used to provide near real-time imaging there are disadvantages to using standard x-ray alone without CT imaging. In particular, while standard x-ray imaging provides very high in spatial resolution, it unfortunately lacks in contrast resolution. For example, standard x-ray cannot visualize a lesion in the liver as the density (contrast) difference between the lesion and the normal tissue is very small.

As noted herein, systems and methods advantageously mitigate a lot of the issues that are encountered by using conventional CT and x-ray imaging by combining an x-ray C-arm and standard CT into a single accessible system. An example improved workflow using the systems described herein may be as follows:

Position patient on a surgical table and anesthetize (note that surgical tables are much better suited for varied positions and comfort/safety of patient than conventional CT tables).

Reposition patient for optimal trajectory.

C-arm with CT mode active brought into place at an appropriate angle.

CT scan to visualize lesion and plan trajectory. Trajectory outlined on workstation in surgical bay with target identified with marker.

Insertion of needle.

Switch to x-ray mode and continual operation of x-ray shots (fluoroscopy) using foot pedal all the time while watching monitor to maintain trajectory. Can overlay CT imaging data with better contrast resolution and trajectory information via cross-registration of images. Can facilitate active surgical navigation, e.g., via integrated robotics.

Switch back to CT mode as needed to adjust trajectory.
Perform CT to confirm that target is reached.
Perform biopsy and retract.

This improved workflow has many advantages. Radiation is reduced by reducing reliance on convention CT imaging which also reduces the need for radiation shielding. Time of the procedure is also drastically reduced (no shuttling in and out of a remote CT imaging room and waiting on radiology). Positioning is made easier and safer using a surgical table during CT imaging. More optimal imaging angles are achieved because of flexibility of C-arm. The C-arm can also be positioned to optimize surgical access. Thus, e.g., a physician is able to maintain control of the biopsy needle the whole time. Anesthesia time is also reduced. CT imaging is achieved without the spatial constraints of a large CT system. Improved surgical navigation and control.

Note that while the above workflow was directed toward interventional radiology similar improvements are applicable to other surgical procedures such as the insertion of pedicle screws and rods in an instrumented spine surgery and brain tumor resection surgery. Notably, the improved systems and methods described herein advantageously allow for a surgeon to be unencumbered by a very large CT yet benefit from the great contrast resolution and 3D spatial resolution of CT while minimizing the radiation and speed up the time of the procedure through the usage of fluoroscopic x-ray.

In other example embodiments, a platform/base component of the hybrid imaging system may be a mobile platform/base, e.g., a same or similar to mobile platform/base. Advantageously, the mobile platform/base may include a motorized mobility assist or type of drive system for facilitating transportation of the system throughout the hospital. In some embodiments, the mobile platform/base may include a multi-directional drive system configured for independently controlling movement in multiple horizontal dimensions, e.g., forward/back and side-to-side. In some embodiments, the multi-directional drive system may be an omni-directional drive system such as a holonomic drive system which includes 3 degrees of freedom and is therefore able to shift from side-to side or strafe diagonally without changing the direction of its wheels. In some embodiments, omni-wheels or mecanum wheels or the like may be utilized to implement the omni-directional drive system. The use of omni-wheels or mecanum wheels may advantageously minimize surface drag and torque. Advantageously an H-drive drivetrain system may be utilized to supply power to each wheel station.

In some embodiments, active safety features may be included which limit or otherwise safeguard against motion of the system (e.g., transport, alignment, and/or scanning type motion) that could potentially harm a patient or cause damage to the system. For example, in some embodiments, sensors such as optical, pressure or resistance based sensors may be utilized to detect proximity of one or more components of the system relative to a patient or object and provide passive feedback (e.g., an alarm or alert) or active feedback (automatic breaking or other motion limitations) based on such proximity detection. In some embodiments, passive and/or active feedback may be subject to manual override.

In example embodiments, a CT scan may be initiated by the hybrid imaging systems disclosed herein, e.g., once the imaging system is configured for a CT exposure mode, e.g., by deploying the CT detector assembly. In some embodiments, a CT scan may utilize an arcuate translation of the C-arm along an arcuate path to rotate the CT detector and radiation generation assemblies (which are positioned opposite one another on opposing ends of the C-arm) around a patient's anatomy. In some embodiments, this type of motion may include rotationally oscillating about an oscillation axis defined by such translation along the arcuate path (e.g., wherein the oscillation axis is perpendicular to both a main axis of rotation of the C-arm and to a transmission axis between the generation and detector assemblies). Thus, in some embodiments, the CT scan may include repeatedly translating the C-arm back and forth along the arcuate path of the C-arm. In further embodiments, the C-arm system may include an axis of rotation for the C-arm (e.g., at a pivot connection point along the arcuate path of the C-arm). Thus in some embodiments a CT scan may be initiated by rotating the c-arm around its axis of rotation thereby orbiting the CT detector and radiation generation assemblies (which are again positioned opposite one another on opposing ends of the C-arm) around a patient's anatomy.

CT scans however are not limited to such simple motions involving a single axis of rotational and/or translational movement. U.S. Pat. No. 7,609,808 to Martin P. Tornai et al., entitled "Application specific emission and transmission tomography" and issued Oct. 27, 2009 (the entire contents of which are incorporated herein by reference) teaches a compact and mobile gantry for 3-dimensional imaging of the a patient's anatomy. In Tornai, the imaging device is mounted relative to a support structure so as to be selectively movable during imaging in three dimensions, including radial movement relative to a rotation axis, rotational movement about the rotation axis, vertical movement parallel to the rotation axis, and pivoting movement about a pivot axis perpendicular to said rotation axis. Notably, Tornai teaches complex scan patterns which may utilize non-traditional CT type motion.

In some embodiments, the proposed hybrid imaging system may implement a CT scan based on a novel complex motion pattern improving on the teachings of Tornai wherein (i) the opposing generation and detector assemblies rotate (orbit) around a main axis of rotation of the C-arm (e.g., at the pivot point connecting to the C-arm) while (ii) the generation and detector assemblies are simultaneously rotationally oscillated about a spinning oscillation axis which is perpendicular to both the main axis of rotation and to a transmission axis between the x-ray generation and detector assemblies (as noted above this oscillation may be implemented by repeatedly translating the C-arm back and forth along the arcuate path of the C-arm). In essence the motion (which may be referred to herein as wobulation) effectively is like that of a see-saw mounted on a merry-go-round, wherein opposing ends of the see-saw represent the generation and detector assemblies. Notably, the rotating and oscillating motions can be independent (e.g., wherein rotational and oscillation positions are independently determined/controlled), or advantageously, in some embodiments, dependent (e.g., wherein rotational positional also determines/controls oscillation position). In some embodiments, the hybrid imaging system may be configured to affect a fixed number of oscillations per rotation during a CT type scan. For example, in some embodiments, the imaging system may be configured to affect two or more oscillations per rotation.

With initial reference to FIG. 1, an example hybrid imaging system 10 is depicted, according to embodiments of the present disclosure. Hybrid imaging system 10 advantageously includes a deployable CT detector assembly 110 (including, e.g., an arcuate CT type detector and an associated data acquisition system (DAS) which may be translated along an arcuate path 112 of the C-arm 100 into a deployed position opposite an x-ray generation assembly 130. When not in use the CT detector assembly may be translated from a deployed position to a non-deployed position thereby exposing a flat panel x-ray type detector 120 for standard x-ray imaging. Notably, a same x-ray generation assembly 130 may be used for both x-ray and CT imaging modes. In some embodiments, the x-ray generation assembly may be reconfigurable depending on the imaging mode (e.g., with different collimators, beam characteristic and/or power profiles for x-ray generation depending on imaging mode). Alternatively, a plurality of interchangeable x-ray generation assemblies may be included each specific for a particular mode. Notably, the hybrid imaging system may further include a movable base 200 configured for transporting and/or aligning the C-arm 100, e.g., by providing for horizontal and/or vertical translational movement thereof 202. Thus, advantageously in some embodiments a drive system 210 may be included which provides omni-directional drive capabilities as described herein. A connecting arm 220 may be used to connect the movable base 200 relative to the c-Arm 100. Notably, the connecting arm may also enable various movement/alignment of the c-Arm 100, e.g., via translational movement of the c-Arm relative to the base and/or via rotational movement of the connecting arm about a pivot point 222 between the base 200 and the connecting arm 220. A connection between the connecting arm 220 and the C-arm 100 may advantageously provide for additional degrees of freedom. For example, the C-arm 100 may be configured to enable translational movement of the C-arm 100 along an arcuate path thereof (e.g., 104). Furthermore the C-arm 100 may be configured to enable rotational movement of the C-arm 100 around an axis of rotation 102 defined by a pivot point between the C-arm 100 and the connecting arm 220. Advantageously, the various degrees of freedom of the hybrid imaging system 10 may be used to facilitate transportation of the hybrid imaging system, alignment relative to a patient and scanning thereof (e.g., by initiation a CT imaging scan via rotating (along one or more axes) the CT detector and x-ray generation assemblies 110 and 130 around a patient's anatomy. For example in some embodiment, a CT imaging scan may include translation of the C-arm 100 along an arcuate path thereof 104, rotation of the C-arm 100 around its rotational axis 102 or a combination of both movements, e.g., wobulation.

With reference now to FIG. 2, a variation 20 of the hybrid imaging system 10 of FIG. 1 is depicted. In particular, FIG. 2 illustrates one alternative mechanism for deploying the CT detection assembly 110. When in a deployed state A the CT detection assembly 110 is positioned over the flat panel detector and aligned with the x-ray source 130. Advantageously, the depicted CT detection assembly 110 in FIG. 2 is configured to translate to the side (e.g., along axis 112) thereby exposing the flat panel detector 120 when the CT detection assembly 110 is in an un-deployed state B. Note, however, that the subject application is not limited to such translational movement and that other deployment motions are possible for example, translating, pivoting, swinging and/or otherwise moving the CT detector assembly into a first position to deploy and translating, pivoting, swinging and/or otherwise moving the CT detector assembly into a second position to un-deploy.

With reference now to FIG. 3, a further variation 30 of the hybrid imaging system 10 of FIG. 1 is depicted. In particular, FIG. 2 illustrates that in some embodiments, the flat panel x-ray detector 120 may be moved rather than the CT detector assembly 110 to effect a change in imaging modes. Thus, e.g., a CT imaging mode may be deployed by translating 122 (or otherwise moving) the flat panel detector 120 to a first position A thereby exposing the CT detector assembly 110. The flat panel detector 120 may then be moved to a second position B aligning the detector 120 with the x-ray source 130 thereby enabling standard x-ray type imaging. Notably, in some embodiments (not depicted) both the CT detection assembly 110 and flat panel detector 120 may move (e.g., either independently or in conjunction with one another) to enable switching between imaging modes. In each case selecting an imaging mode involves aligning a respective detector with a respective x-ray generation source on opposite sides of the C-arm 100.

With reference now to FIG. 4, a further variation 40 of the hybrid imaging system 10 of FIG. 1 is depicted. In particular, FIG. 4 illustrates that in some embodiments, the flat panel x-ray detector 120 may be moved by pivoting it away from the CT detector assembly 110 to effect a change in imaging modes. Thus, e.g., a CT imaging mode may be deployed by pivoting 122 the flat panel detector 120 to a first position A thereby exposing the CT detector assembly 110. The flat panel detector 120 may then be pivoted to a second position B aligning the detector 120 with the x-ray source 130 thereby enabling standard x-ray type imaging. Notably, in some embodiments (not depicted) both the CT detection assembly 110 and flat panel detector 120 may move (e.g., either independently or in conjunction with one another) to enable switching between imaging modes. In each case selecting an imaging mode involves aligning a respective detector with a respective x-ray generation source on opposite sides of the C-arm 100.

Figure 5:
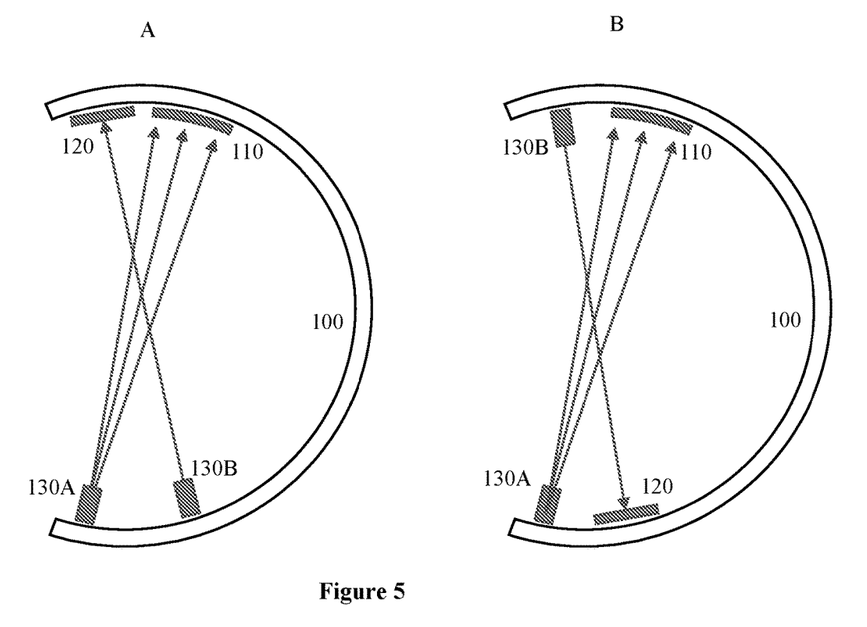
FIGS. 5A and 5B depict respect examples of C-arms including dual detection pathways for different imaging modes, according to embodiments of the present disclosure.

With reference to FIGS. 5A and 5B, the in some embodiments the C-arm 100 may be configured to support dual beam baths (e.g., a first beam bath for x-ray type imaging and a second beam path for CT type imaging). Thus, in some embodiments, such as depicted in FIG. 5A, a first end of the C-arm 100 may include a CT type detector assembly 110 and a flat panel x-ray detector 120 slightly offset from one another along the arcuate surface of the C-arm 100. Corresponding x-ray generation assemblies 130A and 130B (e.g., specific to flat panel x-ray imaging or CT imaging) may be positioned across from their respective detectors at a second end of the C-arm 100 again offset from one another along the arcuate surface of the C-arm 100. In other embodiments, such as depicted in FIG. 5B, respective CT and x-ray type detectors 110 and 120 may be positioned on opposing ends of the C-arm 100, each opposite a corresponding x-ray generation assembly 130A and 130B which is on the same side as the other detector type. FIGS. 5A and 5B illustrate that in some embodiments, active deployment may not be required as a C-arm may be configured to simultaneously include alignment of respective radiation source and detector assemblies for both CT and standard x-ray imaging modes. Thus, in some embodiments, a user need only select the desired imaging mode and initiate a scan (e.g., initiate a CT type scan as described herein).

Figure 6:
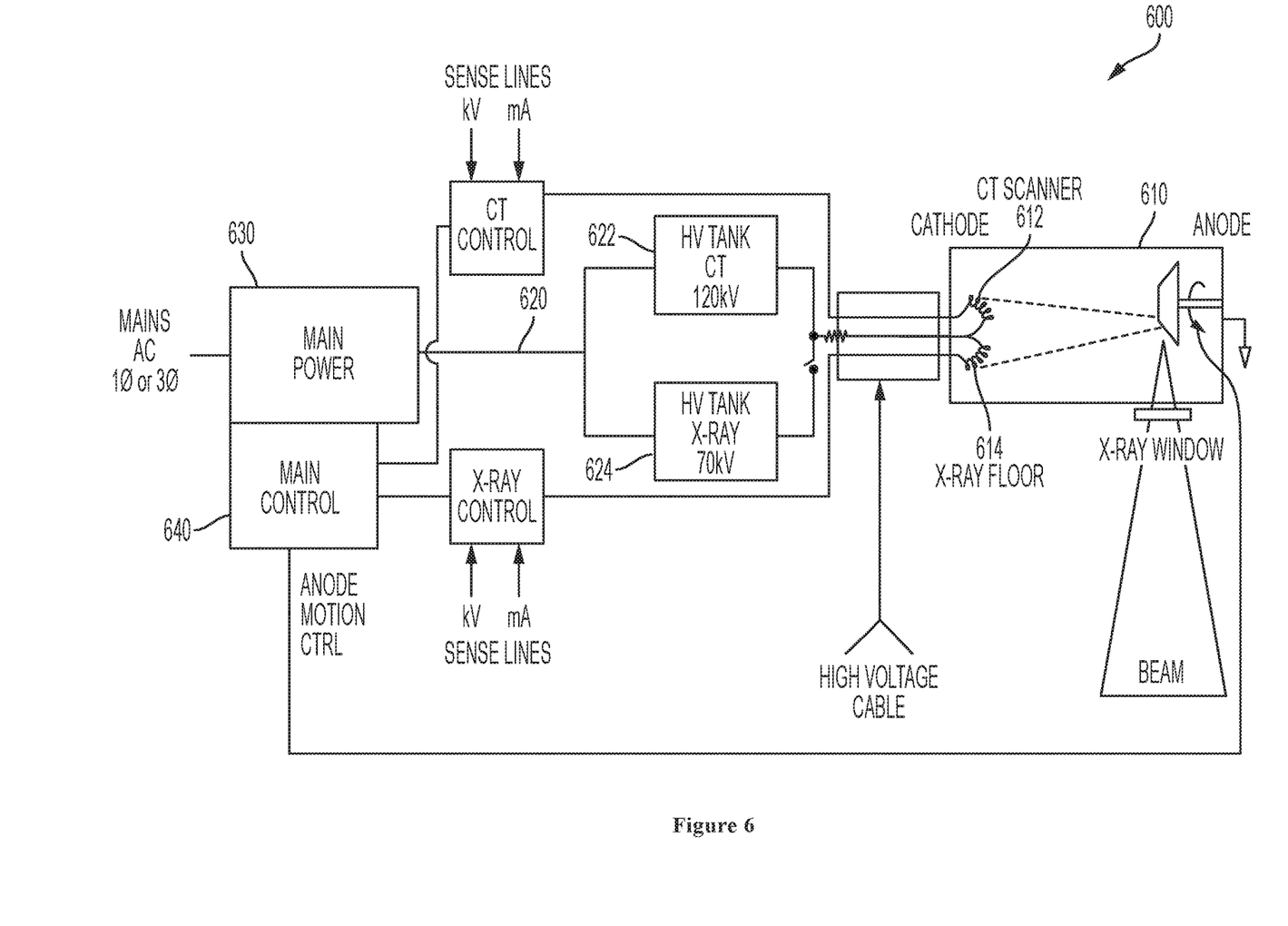
FIG. 6 depicts an exemplary x-ray generation assembly, according to embodiments of the present disclosure.

With reference now to FIG. 6 an exemplary x-ray generation assembly 600 is provided which is able to optimally meet the power profiles for both CT and standard x-ray imaging modes. The x-ray generation assembly 600 includes a common x-ray tube 610 that contains two different filaments (one for CT 612, one for standard x-ray 614) that is powered by a HVPS 620 that has two different high voltage and control circuits 622 and 624 to generate the power profiles for CT and standard x-ray imaging modes respectively. This solution takes up less space and is less expensive and complex. Moreover, it advantageously utilizes common main power 630 and control 640 systems.

Figure 7:
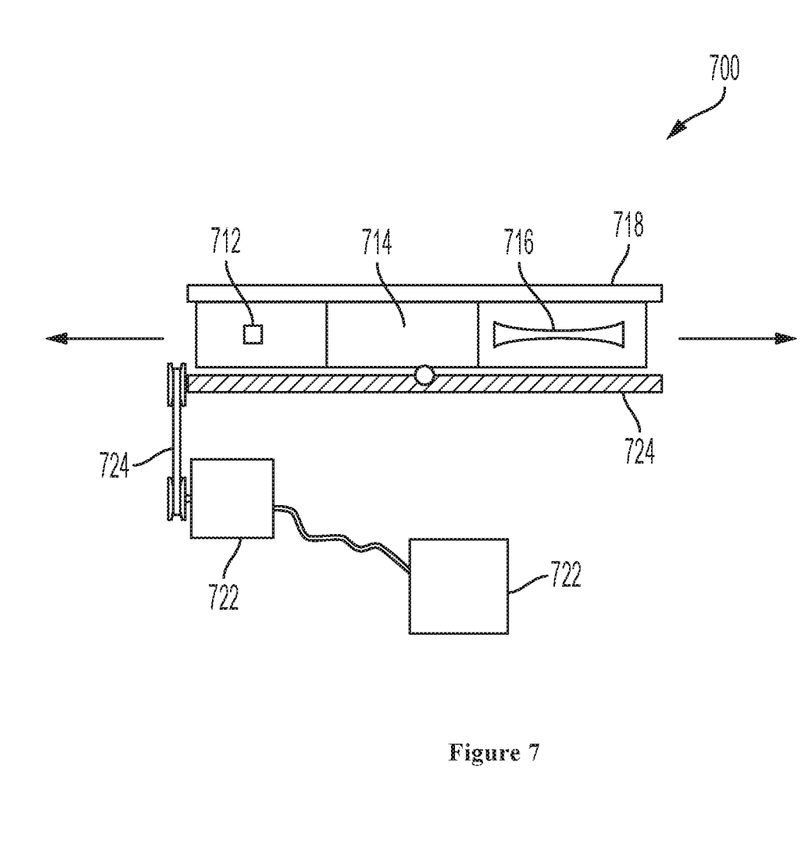
FIG. 7 depicts an exemplary hybrid collimator 700, according to embodiments of the present disclosure.
Figure 8:
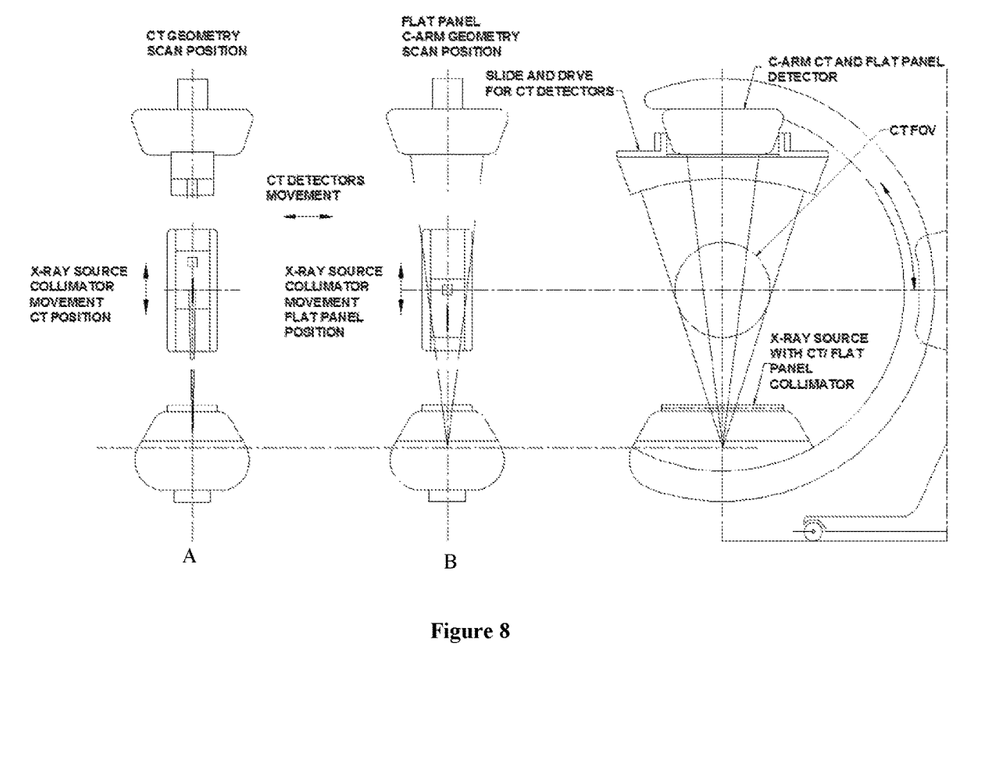
FIG. 8 depicts a hybrid imaging system integrating the hybrid collimator of FIG. 7, according to embodiments of the present disclosure.

With reference now to FIG. 7, an exemplary hybrid collimator 700 is depicted. The hybrid collimator 700 advantageously includes a plurality of different aperture geometries (cutouts) for shaping an x-ray beam including a square-shaped cutout 712 for standard x-ray, a null cutout 714 for blocking the beam and a bowtie-shaped cutout 716 for CT imaging. In the depicted embodiment, the different cutouts are operatively associated with a rail system 718 for changing the cutout depending on the selected imaging mode. The rail system can be driven by a motor drive 720 which controls a motor 722 that drives a precision ball screw 724 via a belt and pulley system 726, thereby translating the rail system 718 and positioning the selected aperture cutout in the beam path. FIG. 8 depicts the hybrid collimator 700 in operation for CT (A) and standard x-ray (B) imaging modes respectively.

Whereas many alterations and modifications of the disclosure will no doubt become apparent to a person of ordinary skill in the art after having read the foregoing description, it is to be understood that the particular embodiments shown and described by way of illustration are in no way intended to be considered limiting. Further, the subject matter has been described with reference to particular embodiments, but variations within the spirit and scope of the disclosure will occur to those skilled in the art. It is noted that the foregoing examples have been provided merely for the purpose of explanation and are in no way to be construed as limiting of the present disclosure.

While the present inventive concept has been particularly shown and described with reference to exemplary embodiments thereof, it will be understood by those of ordinary skill in the art that various changes in form and details may be made therein without departing from the spirit and scope of the present inventive concept as defined by the following claims.

The invention claimed is:

1. A hybrid imaging system comprising an arcuate arm defining a first and a second end, the arcuate arm including one or more x-ray generation assemblies, a first detector assembly for 2D-imaging of a patient and a second detector assembly for CT imaging of the patient, wherein the imaging system includes an internal drive mechanism for rotating the arcuate arm around the patient and wherein the first detector assembly is permanently fixed with respect to a detection region of the arm while the second detector assembly is configured to be retractably deployable over the first detector assembly.

2. The system of claim 1, wherein rotating the arcuate arm includes translating the arcuate arm along an arcuate path.

3. The system of claim 1, wherein the first detector assembly is a flat-panel detector assembly.

4. The system of claim 1, wherein the first detector assembly is configured for fluoroscopic imaging of the patient.

5. The system of claim 1, wherein the second detector assembly is an arcuate detector assembly.

6. The system of claim 5, wherein the detector assembly includes a plurality of arcuate rows of detector elements in a detector array.

7. The system of claim 1, wherein the second detector assembly defines a detection width of greater than 3 cm to enable CT imaging of a wide slice with a single rotational pass.

8. The system of claim 1, wherein the hybrid imaging system is configured to enable selective deployment of the first and second detector assemblies with respect to a detection region of the arm.

9. The system of claim 8, wherein the x-ray generation assemblies are included at an x-ray generation region of the arm wherein the detection region is at a first end of the arm and the x-ray generation region is at a second opposite end of the arm.

10. The system of claim 8, wherein the hybrid imaging system enables selection of an imaging mode whereby a corresponding one of the detector assemblies is deployed with respect to the detection region.

11. The system of claim 1, wherein the retractably deployable detector assembly translates, rotates, pivots, swings or otherwise moves between retracted and deployed positions.

12. The system of claim 11, wherein the retractably deployable detector assembly translates in an arcuate manner along an inner arcuate inner surface of the arm between the retracted and deployed positions.

13. The system of claim 11, wherein the retractably deployable detector assembly translates sideways between retracted and deployed positions.

14. The system of claim 1, wherein both detector assemblies are retractably deployable.

15. The system of claim 14, wherein the first and second detector assemblies are fixed relative to one another and movable between a first position where one of the detector assemblies is deployed and a second position where the other detector assembly is deployed.

16. The system of claim 14, wherein the first and second detector assemblies are fixed side-by-side relative to one another and are configured for sideways translation thereof to enable selective deployment of one or the other of the detector assemblies.

17. The system of claim 1, wherein the one or more x-ray generation assemblies include a hybrid x-ray generation assembly which includes a hybrid collimator enabling selective switching back and forth between 2D and CT exposure modes.

18. The system of claim 1, further including an omni-drive system.

19. The system of claim 1, the internal drive mechanism is configured to provide for wobulation.

20. A hybrid imaging system comprising an arcuate arm defining a first and a second end, the arcuate arm including one or more x-ray generation assemblies, a first detector assembly for 2D-imaging of a patient and a second detector assembly for CT imaging of the patient, wherein the imaging system includes an internal drive mechanism for rotating the arcuate arm around the patient and wherein a first x-ray generation assembly includes a first collimator configured for a 2D exposure mode and a second x-ray generation assembly includes a second collimator configured for a CT exposure mode.

* * * * *